(12) United States Patent
Nam et al.

(10) Patent No.: US 11,342,070 B2
(45) Date of Patent: *May 24, 2022

(54) DEVICE AND METHOD FOR MONITORING HEALTH STATE OF USER, AND DEVICE FOR MANAGING HEALTH STATE OF USER

(71) Applicant: SAMSUNG ELECTRONICS CO., LTD., Suwon-si (KR)

(72) Inventors: Jung Yong Nam, Hwaseong-si (KR); Sang Kyu Kim, Yongin-si (KR); Jung Mok Bae, Seoul (KR); So Young Lee, Daejeon (KR); Joon Hyung Lee, Yongin-si (KR); Ki Young Chang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 219 days.

This patent is subject to a terminal disclaimer.

(21) Appl. No.: 16/729,592

(22) Filed: Dec. 30, 2019

(65) Prior Publication Data

US 2020/0129131 A1 Apr. 30, 2020

Related U.S. Application Data

(63) Continuation of application No. 15/358,794, filed on Nov. 22, 2016, now Pat. No. 10,548,536.

(30) Foreign Application Priority Data

Feb. 3, 2016 (KR) .................... 10-2016-0013570

(51) Int. Cl.
*A61B 5/145* (2006.01)
*G16H 40/60* (2018.01)
(Continued)

(52) U.S. Cl.
CPC ......... *G16H 40/60* (2018.01); *A61B 5/14546* (2013.01); *A61B 5/4866* (2013.01);
(Continued)

(58) Field of Classification Search
CPC . A61B 5/7278; A61B 5/14546; A61B 5/4866; A61B 5/7275; A61B 5/746; G06F 19/30; G09B 7/00
See application file for complete search history.

(56) References Cited

U.S. PATENT DOCUMENTS

| 5,075,101 A | 12/1991 | Siguel |
| 8,883,086 B2 | 11/2014 | Bae et al. |
(Continued)

FOREIGN PATENT DOCUMENTS

| JP | 2004-358052 A | 12/2004 |
| JP | 5022285 B2 | 9/2012 |
(Continued)

OTHER PUBLICATIONS

OKeefe et al., "Postprandial Hyperglycemia/Hyperlipidema (Postprandial Dysmetabolism) is a Cardiovascular Risk Factor", Amer Jour of Cariology, pp. 899-904, 2007.
(Continued)

*Primary Examiner* — Eric F Winakur
(74) *Attorney, Agent, or Firm* — Sughrue Mion, PLLC

(57) ABSTRACT

A device and method for monitoring a user's health state by continuously measuring data on triglycerides of the user and a device for managing the user's health state are disclosed. According to an embodiment, a user health state monitoring device includes a measurement unit configured to continuously measure a triglyceride concentration level of the user for a predetermined period; an analysis unit configured to analyze a graph showing the triglyceride concentration level to acquire analytical information; and a monitoring unit
(Continued)

configured to monitor the user's health state based on the acquired analytical information.

17 Claims, 11 Drawing Sheets

(51) Int. Cl.
| | |
|---|---|
| *A61B 5/00* | (2006.01) |
| *G16H 50/20* | (2018.01) |
| *G16H 40/63* | (2018.01) |
| *G16H 70/20* | (2018.01) |
| *G16H 15/00* | (2018.01) |
| *G09B 19/00* | (2006.01) |
| *G09B 7/00* | (2006.01) |

(52) U.S. Cl.
CPC .......... *A61B 5/7275* (2013.01); *A61B 5/7278* (2013.01); *G16H 15/00* (2018.01); *G16H 40/63* (2018.01); *G16H 50/20* (2018.01); *G16H 70/20* (2018.01); *A61B 5/746* (2013.01); *G09B 7/00* (2013.01); *G09B 19/0092* (2013.01)

(56) References Cited

U.S. PATENT DOCUMENTS

| | | |
|---|---|---|
| 2007/0088228 A1 | 4/2007 | Uchida et al. |
| 2009/0246289 A1 | 10/2009 | Superko et al. |
| 2012/0191469 A1 | 7/2012 | Akradi |
| 2015/0072366 A1 | 3/2015 | Deutz et al. |
| 2015/0193588 A1 | 7/2015 | Nemoto et al. |
| 2016/0328991 A1 | 11/2016 | Simpson et al. |

FOREIGN PATENT DOCUMENTS

| | | |
|---|---|---|
| JP | 2013-97403 A | 5/2013 |
| JP | 5667814 B2 | 2/2015 |
| KR | 10-2006-0037536 A | 5/2006 |
| KR | 10-1239340 B1 | 3/2013 |
| KR | 10-1553908 B1 | 9/2015 |
| KR | 10-2015-0110412 A | 10/2015 |

OTHER PUBLICATIONS

Eberly et al., Relation of Triglyceride Levels, Fasting and Non-fasting, to Fatal and Nonfatal Coronary Heart Disease, Arch Intern Med, vol. 163, pp. 1077-1083, 2003.

Nakamura et al., "Postprandial hyperlipidemia as a potential residual risk factor", Jour Cardiology, pp. 335-339, 2015.

DEVICE AND METHOD FOR MONITORING HEALTH STATE OF USER, AND DEVICE FOR MANAGING HEALTH STATE OF USER

CROSS-REFERENCE TO RELATED APPLICATION

This application is a Continuation Application of U.S. application Ser. No. 15/358,794, filed Nov. 22, 2016, which claims priority from Korean Patent Application No. 10-2016-0013570, filed on Feb. 3, 2016, in the Korean Intellectual Property Office, the disclosure of which is incorporated herein by reference in its entirety.

BACKGROUND

1. Field

Apparatuses and methods consistent with exemplary embodiments relate to monitoring a user's health state related to triglycerides through analysis of data on triglycerides.

2. Description of Related Art

A triglyceride level in blood is measured to predict a risk of getting an arteriosclerotic disease and is also used as a standard for determining a metabolic syndrome together with blood glucose, blood pressure, waist measurement, and a high-density lipoprotein (HDL) cholesterol level. Generally, the triglyceride level in blood is measured by a blood test and fasting for 10-12 hours before the test is required. The triglyceride level is recommended to be maintained at a level less than or equal to 150 mg/dL. A high concentration of triglycerides in blood is known to cause arteriosclerosis and cardiovascular disorders together with cholesterol.

Triglycerides exist in the forms of various types of lipoproteins, and most of them are included in chylomicrons and very low density lipoproteins (VLDLs). Chylomicrons originate from the small intestine, increase after food is ingested, and decrease due to actions of enzymes such as a lipase. VLDLs are formed in liver and are normally known to be maintained at a constant level.

Although it has been standard to measure triglycerides after fasting for 10 to 12 hours, the effectiveness has been questioned since most people are in postprandial states most of the time. Accordingly, there have been attempts to measure and utilize postprandial triglyceride levels, but there are no clear criteria and methods therefor.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a device for monitoring a health state of a user, the device comprising one or more processors implementing: a measurement unit configured to continuously measure a triglyceride concentration level of the user for a predetermined period; an analysis unit configured to analyze a graph showing the triglyceride concentration level to acquire analytical information; and a monitoring unit configured to monitor the user's health state based on the acquired analytical information.

The analytical information may include at least one of maximum values, minimum values, a number of peaks, intervals between the peaks, areas under the graph, and slopes of the graph.

The monitoring unit may monitor a trend of changing the triglyceride concentration level of the user based on trends of the maximum value or the minimum value during the predetermined period.

The monitoring unit may determine any one or any combination of the minimum values, the maximum values, an average of the minimum values, an average of the maximum values, and median values of the minimum values and the maximum values as a triglyceride level of the user and determines abnormality of triglyceride metabolism of the user by comparing the user's triglyceride level with a preset reference value.

The monitoring unit may compare any one of the minimum values, the maximum values, the average of the minimum values, the average of the maximum values, and the median values of the minimum values and the maximum values with the user's triglyceride level measured in advance during fasting and, as a result of the comparison, may determine any one value that satisfies a predetermined standard as the user's triglyceride level.

The monitoring unit may determine a diet pattern of the user based on at least one of the number of the peaks and the intervals between the peaks and monitors the user's health state based on the determined diet pattern.

The monitoring unit may provide a question and answer (Q&A) session about a diet pattern with the user based on the determined diet pattern, analyze a correlation between responses of the user and the user's triglyceride level, and monitor the user's health state.

The monitoring unit may compare the graph showing the triglyceride concentration level of the user during the predetermined period with a reference graph showing a triglyceride concentration level of a healthy person or detects changes in the number of peaks and the intervals between the peaks acquired for each predetermined section, and may determine whether the graph showing the triglyceride concentration level of the user has a normal pattern or an abnormal pattern.

The monitoring unit may determine that triglyceride metabolism of the user is abnormal when the graph showing the triglyceride concentration level of the user is determined to have the abnormal pattern.

The monitoring unit may determine a decreasing rate of the triglyceride concentration level based on a negative slope of the graph showing the triglyceride concentration level of the user.

The predetermined period may include at least one of days, weeks, months, and years; and the analysis unit may analyze the graph showing the triglyceride concentration level by dividing the graph into two or more sections which are shorter than the predetermined period.

According to an aspect of another exemplary embodiment, there is provided a method for monitoring a health state of a user including: continuously measuring a triglyceride concentration level of the user for a predetermined period; analyzing a graph showing the triglyceride concentration level to acquire analytical information; and monitoring the user's health state based on the acquired analytical information.

The analytical information may at least one of maximum values, minimum values, a number of peaks, intervals between the peaks, areas under the graph, and slopes of the graph.

The monitoring may include monitoring a trend of changing the triglyceride concentration level of the user based on trends of the maximum values or the minimum values during the predetermined period.

The monitoring may determine any one or any combination of the minimum values, the maximum values, an average of the minimum values, an average of the maximum values, and median values of the minimum values and the maximum values as a triglyceride level of the user and determines abnormality of triglyceride metabolism of the user by comparing the user's triglyceride level with a preset reference value.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
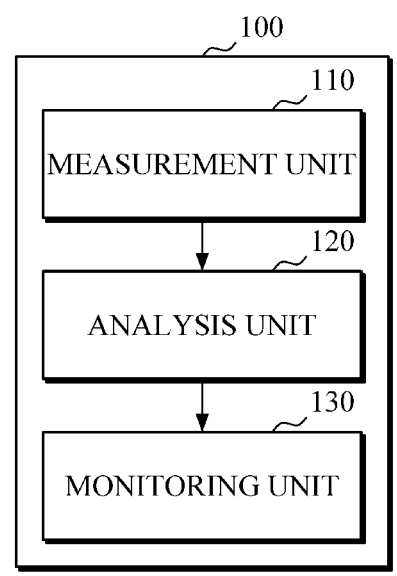
FIG. 1 is a block diagram illustrating a device for monitoring a user's health state according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

FIG. 1 is a block diagram illustrating a user health state monitoring device 100 according to an exemplary embodiment.

Referring to FIG. 1, the user health state monitoring device 100 includes a measurement unit 110, an analysis unit 120, and a monitoring unit 130. The measurement unit 110, the analysis unit 120, and the monitoring unit 130 may be implemented by one or more processors.

The measurement unit 110 may continuously measure data on triglycerides of a user during a predetermined period. Here, although the predetermined period may be set as days, weeks, months, and years, etc., the predetermined period is not limited thereto and may be set as various periods according to a user's health state or the purpose of measurement. For example, the predetermined period may be set such that triglycerides are measured at shorter intervals when user's health is not in a good state and may be set as a relatively longer period when attempting to collect long-term data. Here, the phrase "continuously measuring" refers to measuring in real time during a predetermined period as well as measuring at predetermined intervals (e.g. once per hour, once per day, once per week, once per month, etc.).

For example, the measurement unit 110 may measure data on triglycerides of the user by periodically measuring a concentration of triglycerides in a user's blood serum from the user's blood. In another example, when a measurement device is worn on a part of the user's body or the user is indirectly connected to the measurement device, the measurement unit 110 may measure the data on triglycerides in real time or periodically through the measurement device. Here, the measurement device may be embedded in the user health state monitoring device 100 or may be a separate hardware device.

The analysis unit 120 may analyze a graph showing triglyceride concentrations based on the data on triglycerides of a user continuously measured by the measurement unit 110 during a predetermined period to acquire analytical information, which the monitoring unit 130 uses in monitoring the user's health state. Here, the analytical information may include maximum values, an average of the maximum values, minimum values, an average of the minimum values, median values of the minimum values and the maximum values, the number of peaks, intervals between the peaks, areas under graphs, and slopes of the graphs, etc. of the measured data on triglycerides of the user, but the analytical information that may be acquired is not limited thereto. The maximum values may correspond to a maximum triglyceride concentration level obtained from an entire measurement period or a maximum triglyceride concentration level in each graph generated during every predetermined measurement period. The minimum values may correspond to a minimum triglyceride concentration level obtained from an entire measurement period or a minimum triglyceride concentration level in each graph generated during every predetermined measurement period. The median values may be a value resulting from dividing sums of the maximum values and the minimum values in half, or may be an average value of the maximum values or an average value of the minimum values. The term "peak" may refer to a maximum value at an instant when a positive slope of a graph changes back to a negative slope.

The monitoring unit 130 may monitor a user's health state based on the analytical information acquired by the analysis unit 120. The user's health state monitored by the monitoring unit 130 may include the user's diet pattern, metabolic state of triglycerides, risk of diseases, etc., and the user's diet pattern may include a number of times of food intake, whether food is ingested regularly, whether a regular amount of food is ingested, whether overeating has occurred, etc. The diseases may include a metabolic syndrome related to triglycerides, an arteriosclerotic disease, a hypertriglyceridemia, etc.

Accordingly, without having to keep fasting to measure data on triglycerides, a user of the user health state monitoring device 100 may check his or her health state only by continuously measuring and analyzing data on triglycerides of the user through the user health state monitoring device 100 while keeping a daily life pattern.

Figure 4:
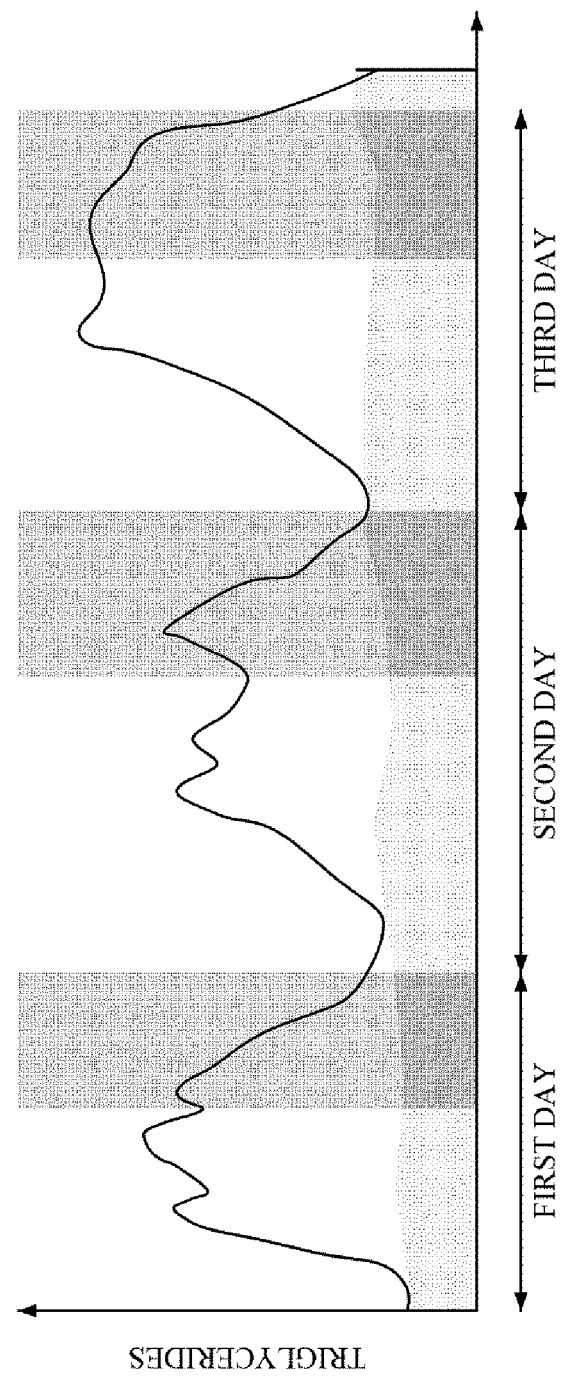
FIG. 4 is a view illustrating a graph based on data on triglycerides of a user according to an exemplary embodiment.

The monitoring unit 130 may use an area under a graph showing triglyceride concentrations to monitor a triglyceride intake pattern that shows an amount of triglycerides ingested by the user. Since an area under a graph of data on triglycerides during a predetermined period is proportional to an amount of triglycerides ingested during the predetermined period, the monitoring unit 130 may monitor the user's triglyceride intake pattern based on an increase or a decrease of the area under the graph showing triglyceride concentrations of the user. Referring to FIG. 4, since an area under the graph showing triglyceride concentrations on a third day is greater than those on a first day and a second day, it can be determined that the triglyceride intake amount of the user has increased on the third day compared to the first day and the second day and that the triglyceride intake pattern shows an increasing trend.

The monitoring unit 130 may monitor a trend of changing triglyceride concentration of the user based on trends of the maximum values or the minimum values during a predetermined period. According to an aspect, the analysis unit 120 may acquire a maximum value or a minimum value in each graph generated during every predetermined period, and the monitoring unit 130 may detect trends of changing maximum values or the minimum values based on an increase or a decrease of the acquired maximum values or minimum values. The monitoring unit 130 may determine that a concentration of triglycerides in the user's body is increasing when the maximum values or the minimum values are detected to have a continuously increasing trend and may determine that the concentration of triglycerides in the user's body is decreasing when the maximum values or the minimum values show a continuously decreasing trend. However, since an increase/decrease of the maximum values or minimum values of triglycerides may occur temporarily, the monitoring unit 130 may determine that the user's triglyceride concentration has an increasing or decreasing trend only when the increase or decrease of the maximum values or the minimum values is continued for a period that is longer than a predetermined reference period.

The monitoring unit 130 may determine any one of the acquired minimum values, maximum values, an average of the minimum values, an average of the maximum values, and median values of the minimum values and the maximum values as a user's triglyceride level and may determine an abnormality of triglyceride metabolism of the user by comparing the user's triglyceride level with a preset reference value.

For example, the monitoring unit 130 may determine a minimum value in a graph showing triglyceride concentrations as a triglyceride level. Since a generally known technology for determining a state of triglyceride metabolism makes a determination using a triglyceride level during fasting, and the triglyceride level during fasting is likely to be close to the minimum value in the graph showing triglyceride concentrations, the monitoring unit 130 may determine the minimum value in the graph showing triglyceride concentrations as the triglyceride level and determine the state of triglyceride metabolism based on the triglyceride level.

In another example, the monitoring unit 130 may compare any one of the acquired minimum values, maximum values, an average of the minimum values, an average of the maximum values, and median values of the minimum values and the maximum values with the user's triglyceride level measured in advance during fasting and, as a result of the comparison, may determine any one value that satisfies a predetermined standard as the user's triglyceride level.

The monitoring unit 130 may preset a reference value to be used in determining whether triglyceride metabolism of the user is abnormal. For example, when the user is determined to be normal, the monitoring unit 130 may set minimum values, maximum values, an average of the minimum values, an average of the maximum values, or an average value of each of the median values of the minimum values and the maximum values in the graph showing triglyceride concentrations generated by a continuous measurement as the reference values. The reference values set by the monitoring unit 130 based on the average values may more accurately show the user's personal characteristics with an increasing period in which the user is determined and measured to be normal. Accordingly, the monitoring unit 130 may personalize the setting of the reference values corresponding to personal characteristics of a user of the user health state monitoring device 100.

In another example, the monitoring unit 130 may set the reference values based on research findings of research institutes and clinical trial results of pharmaceutical companies and clinics or may set values (e.g. 150 mg/dL) determined and recommended by the corresponding institutes as the reference values.

In still another example, the monitoring unit 130 may set the reference values based on triglyceride levels of several normal people measured during fasting. For example, the monitoring unit 130 may set an average of the triglyceride levels of the several normal people measured during fasting or any one value among minimum values, maximum values, average values, and median values that fits a situation acquired by applying the exemplary embodiment to the several normal people as the reference value. For example, when a determined user's triglyceride level is a minimum value, corresponding to this, minimum values of the normal people or an average value of the minimum values may be set as the reference value. However, exemplary embodiments are not limited to the examples above.

The monitoring unit 130 may compare a determined user's triglyceride level with a preset reference value and determine whether triglyceride metabolism of the user is abnormal. For example, when any one of minimum values, maximum values, an average of the minimum values, an average of the maximum values, and median values of the minimum values and the maximum values of a graph showing triglyceride concentrations is determined as the user's triglyceride level, and when minimum values, maximum values, an average of the minimum values, an average of the maximum values, or an average of median values of the minimum values and the maximum values of a graph showing triglyceride concentrations of the user's normal state is set as the reference value, the triglyceride metabolism of the user may be determined to be abnormal when a difference between the user's triglyceride level and the reference value corresponding to the level is beyond a permissible range.

In another example, when a minimum value in a graph showing triglyceride concentrations is determined as a user's triglyceride level and when a value recommended by a medical institution is set as a reference value, the monitoring unit 130 may determine the user's health to be in a normal state in which the minimum value is less than or equal to 150 mg/dL. The monitoring unit 130 may determine that the state of triglyceride metabolism of the user is at a warning level or a risk level according to the extent to which the minimum value exceeds the reference value (e.g., 150 mg/dL).

In addition, the monitoring unit 130 may compare the determined triglyceride level with the set reference value and may determine a risk for the user getting a disease related to triglycerides based on the extent to which the difference between the two values deviates from a predetermined permissible range. For example, the monitoring unit 130 may determine that the risk for the user getting a disease related to triglyceride level increases as a difference between the triglyceride level and the reference value increases.

The monitoring unit 130 may compare any one of minimum values, maximum values, an average of the minimum values, an average of the maximum values, and median values of the minimum values and the maximum values acquired by the analysis unit 120 with a user's triglyceride level measured in advance during fasting and, as a result of the comparison, may determine any one value that satisfies a predetermined standard as the user's triglyceride level. The monitoring unit 130 may preset a standard in which, when a value acquired by the analysis unit 120 is compared with a user's triglyceride level measured in advance during fasting, the value subject to the comparison is determined as the user's triglyceride level when a difference between the compared values is within a set range.

As an example of determining the user's triglyceride level, the monitoring unit 130 may compare a minimum value acquired when the user is in a normal state with a user's triglyceride level measured in advance during fasting, may check that the two values are similar, and may determine the acquired minimum value as the user's triglyceride level. In addition, the monitoring unit 130 may compare minimum values, maximum values, an average of the minimum values, an average of the maximum values, and median values of the minimum values and the maximum values acquired when the user is in a normal state with the user's triglyceride level measured in advance during fasting, check that the value is within a predetermined range, and may determine the value confirmed to be within the predetermined range as the user's triglyceride level.

According to an aspect, the monitoring unit 130 may detect a risk for the user getting diseases related to triglycerides such as metabolic syndrome, arteriosclerotic disease, hypertriglyceridemia, etc. based on the user's triglyceride level. According to another aspect, when the user's triglyceride level does not satisfy a recommended reference range during fasting, the monitoring unit 130 may detect that the user's triglyceride metabolism is abnormal. Since a triglyceride level measured during fasting is recommended to be maintained to be equal to or less than 150 mg/dL, the monitoring unit 130 may determine the determined triglyceride level that is less than 150 mg/dL as being "normal," determine the determined triglyceride level that is within 150 to 199 mg/dL as being at a "warning level," and determine the determined triglyceride level that is equal to or higher than 200 mg/dL as being at "risk level."

The monitoring unit 130 may determine the user's diet pattern based on at least one of data sets including the number of peaks and intervals between the peaks in a graph showing triglyceride concentrations and may monitor the user's health state based on the determined diet pattern. According to an aspect, the monitoring unit 130 may determine a number of times of food intake of the user based on the number of peaks in the a graph showing triglyceride concentrations, may determine time intervals in which the user has ingested food based on the intervals between the peaks, and may determine whether the user regularly ingests food. The monitoring unit 130 may determine that there is an abnormality in the user's diet pattern when the number of times of food intake determined based on the number of peaks in the graph showing triglyceride concentrations is greater than a recommended number of times or when the intervals between food intakes determined based on the intervals between peaks in the graph showing triglyceride concentrations is shorter than a recommended interval between food intakes. For example, when the number of peaks exceeds three per day (24 hours) or the intervals between peaks is less than four hours, the monitoring unit 130 may determine that there is an abnormality in the user's diet pattern. However, the criteria for determination are not limited thereto.

The monitoring unit 130 may have a question and answer (Q&A) session about a diet pattern with the user based on the determined diet pattern and analyze a correlation between responses of the user and the user's triglyceride level to monitor the user's health state. For example, the monitoring unit 130 may provide a graphic user interface to display questions on a screen and receive answers which are input by the user in response to the questions. The monitoring unit 130 may determine the number of times of food intake of the user based on the number of peaks in the graph showing triglyceride concentrations of the user, and may provide a message that inquires whether the determined number of times of food intake matches an actual number of times of food intake of the user while providing the user with the number of times of food intake determined by the monitoring unit 130. When the user confirms that the number of times of food intake included in the message matches the actual number of food intake, the monitoring unit 130 may determine the user's health state to be normal. When the user confirms that the two numbers does not match, the monitoring unit 130 may determine the user's health state including triglyceride metabolism to be abnormal.

The monitoring unit 130 may compare a graph showing triglyceride concentrations during a predetermined period with a graph showing triglyceride concentrations of a normal person or detect changes in a number of peaks and intervals between peaks acquired for each section to determine whether the graph showing triglyceride concentrations has a normal pattern or an abnormal pattern. According to an aspect, the monitoring unit 130 may transmit the graph showing the user's triglyceride concentrations to a terminal, or the like used by a doctor and request the doctor to determine whether the user's graph has a normal pattern or an abnormal pattern. According to another aspect, the monitoring unit 130 may determine the graph showing triglyceride concentrations of the user as having an abnormal pattern when the number of peaks exceeds three per day (i.e. 24 hours) or the intervals between peaks is less than four hours. However, the criteria for determination are not limited thereto. According to still another aspect, the graph showing triglyceride concentrations of the user may be determined as abnormal when a start point of the graph showing triglyceride concentrations does not correspond to a minimum point and the graph includes several oscillations when the graph showing triglyceride concentrations is monitored for a day.

When the graph showing triglyceride concentrations of the user shows an abnormal pattern as a result of determination, the monitoring unit 130 may determine that the user's triglyceride metabolism is abnormal and may provide the name of a disease related to triglyceride from which the user suffers through measuring, analyzing, and monitoring data on triglycerides for a long period.

The monitoring unit 130 may determine efficiency in triglyceride clearance of the user based on a negative slope of the graph showing triglyceride concentrations. When the negative slope of the graph showing triglyceride concentrations of the user is lower than that of a graph showing healthy triglyceride concentrations, the monitoring unit 130 may determine that there is an abnormality in the user's triglyceride metabolism. The graph showing healthy triglyceride concentrations may include a sample graph of data on triglycerides measured from a healthy normal person in clinics or research institutes, etc., and according to another aspect, may include a graph obtained by measuring data on triglycerides of a user in advance when the user using the user health state monitoring device 100 is healthy.

The analysis unit 120 may generate a graph showing triglyceride concentrations based on data on triglycerides continuously measured during a predetermined period and analyze the graph showing triglyceride concentrations by dividing the graph into two or more analysis sections that are shorter than the predetermined period. For example, when the predetermined period is a week, the analysis unit 120 may generate a graph showing triglyceride concentrations based on data on triglycerides measured during the week and analyze the graph showing triglyceride concentrations by setting a day as an analysis section, i.e., by dividing the week into seven sections. In another example, the analysis unit 120 may analyze a graph showing triglyceride concentrations generated by measuring triglycerides for a year by dividing an analysis section thereof into months, i.e., by dividing the analysis section into twelve sections. According to another aspect, the analysis unit 120 may set the number of divided sections according to the user's health state or the purpose of measurement. For example, the analysis unit 120 may set one hour as one analysis section and analyze a graph showing triglyceride concentrations obtained after measuring for a week by dividing the graph into 168 sections.

Figure 2:
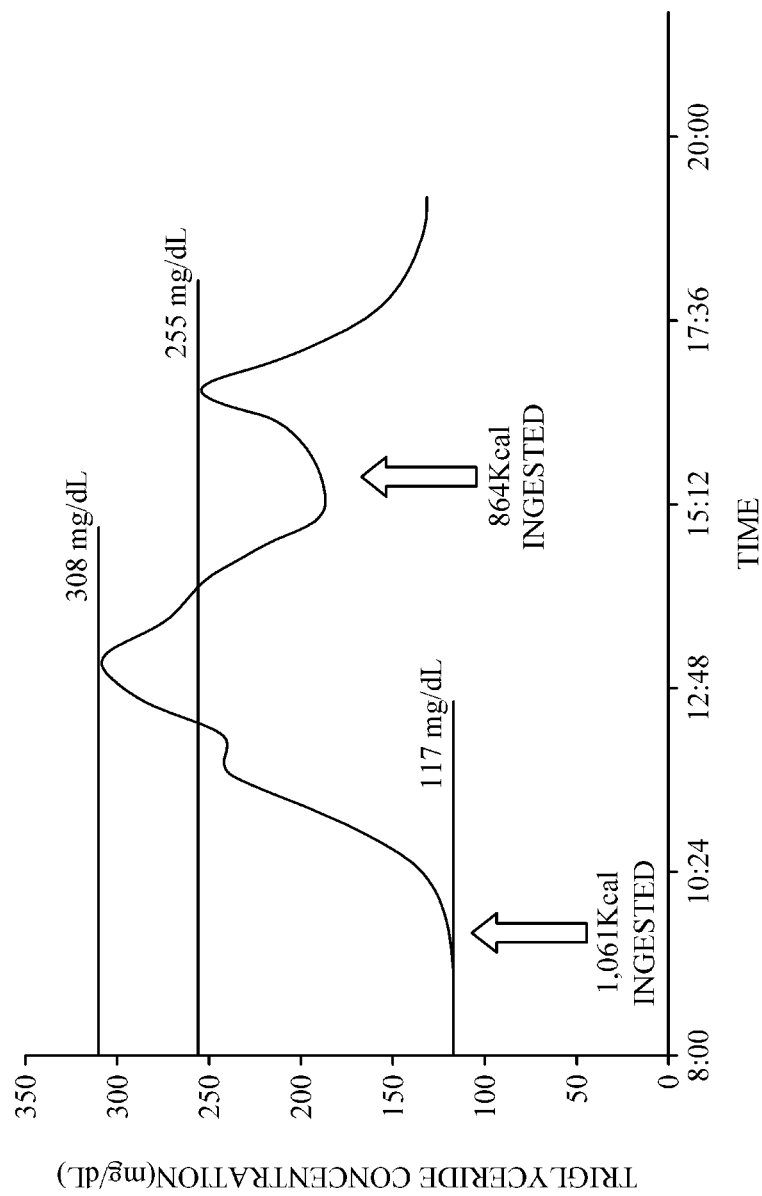
FIG. 2 is a view illustrating a graph showing triglyceride concentrations when a user's health state is normal according to an exemplary embodiment.

FIG. 2 is a view illustrating a graph showing triglyceride concentrations when a user's health state is normal according to an exemplary embodiment.

Referring to FIGS. 1 and 2, the analysis unit 120 may analyze a graph showing triglyceride concentrations of a user as in FIG. 2 and acquire analytical information including that the maximum value in the graph showing triglyceride concentrations of the user is 308 mg/dL, the minimum value therein is 117 mg/dL, and the number of peaks therein is two.

Since the number of peaks in the acquired graph showing triglyceride concentrations is two, the monitoring unit 130 may determine that the user has ingested food twice during twelve hours (08:00 to 20:00). According to an aspect, the monitoring unit 130 may set the user's ingesting food three times from 8 a.m. to 8 p.m. as a normal diet pattern, and since the user in FIG. 2 has ingested food only twice from 8 a.m. to 8 p.m., the monitoring unit 130 may determine the user's diet pattern as an abnormal diet pattern.

In addition, since the start point of the graph showing triglyceride concentrations of the user corresponds to a minimum value, the minimum value is 117 mg/dL, and this is a lower level than 150 mg/dL which is a recommended triglyceride level during fasting, the monitoring unit 130 may determine that the user's triglyceride metabolism is normal.

Figure 3:
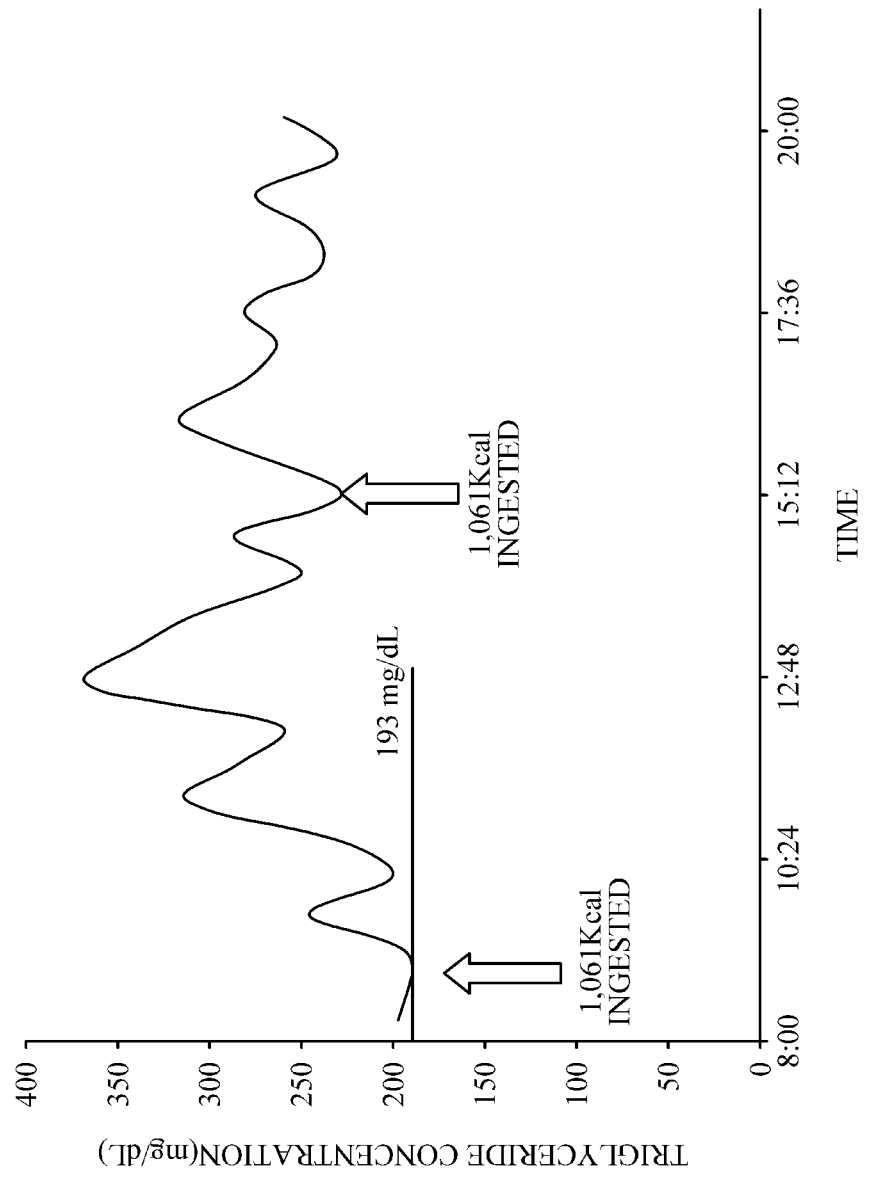
FIG. 3 is a view illustrating a graph showing triglyceride concentrations when a user's health state is abnormal according to an exemplary embodiment.

FIG. 3 is a view illustrating a graph showing triglyceride concentrations when a user's health state is abnormal according to an exemplary embodiment.

Referring to FIGS. 1 and 3, the analysis unit 120 may analyze a graph showing triglyceride concentrations of the user as in FIG. 3 and acquire analytical information that the minimum value in the graph showing triglyceride concentrations of the user is 193 mg/dL. Since this is a higher level than 150 mg/dL, which is a recommended triglyceride level during fasting, the monitoring unit 130 may determine that the user's triglyceride metabolism is abnormal and determine that a risk of getting diseases related to triglycerides such as hypertriglyceridemia is high.

In addition, the monitoring unit 130 may obtain information from the user that the actual number of times of food intake is twice a day and may determine that the graph showing triglyceride concentrations of the user in FIG. 3 has an abnormal pattern since the number of peaks in the graph showing triglyceride concentrations of the user of FIG. 3 is greater than two and the triglyceride concentrations oscillate in short intervals.

FIG. 4 is a view illustrating a graph based on data on triglycerides of a user according to an exemplary embodiment.

Referring to FIGS. 1 and 4, the measurement unit 110 may continuously measure data on triglycerides of a user during three days, and the analysis unit 120 may analyze the graph showing triglyceride concentrations in FIG. 4 and determine an area under the graph for each day (i.e. 24 hours). In case of FIG. 4, since an area under the graph on the third day is relatively large compared to those on the first day and the second day, the monitoring unit 130 may determine that the amount of triglyceride intake of the user has increased. In addition, since it can be recognized that the first peak point of the third day is greater than the other peak points, the monitoring unit 130 may determine that the user has overeaten at the first food intake on the third day.

Figure 5:
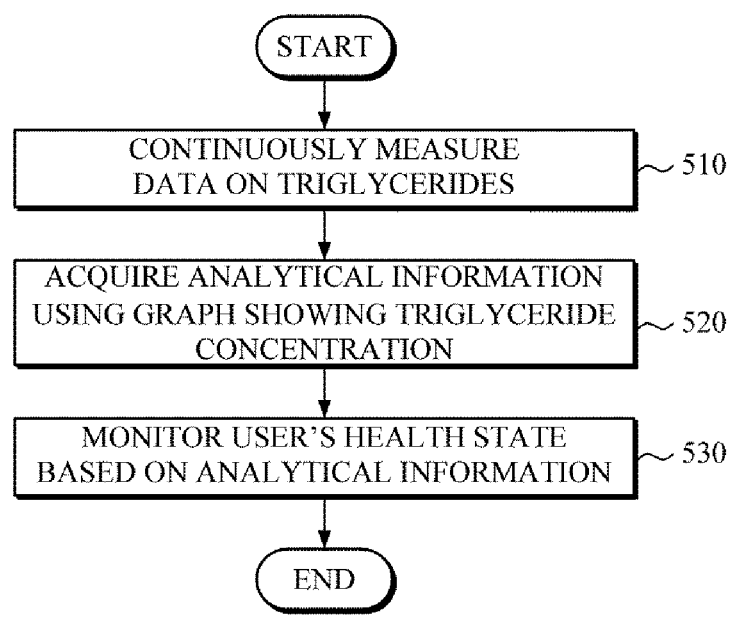
FIG. 5 is a flowchart illustrating a method for monitoring a user's health state according to an exemplary embodiment.

FIG. 5 is a flowchart of a method for monitoring a user's health state according to an exemplary embodiment.

The method for monitoring a user's health state of FIG. 5 is an exemplary embodiment performed by the user health state monitoring device 100 of FIG. 1.

The user health state monitoring device 100 may continuously measure data on triglycerides of a user during a predetermined period (operation S510) and analyze a graph showing triglyceride concentrations based on data on triglycerides of the user to acquire analytical information (operation S520).

After the analytical information is acquired, the user health state monitoring device 100 may monitor the user's health state based on the acquired analytical information (operation S530).

Figure 6:
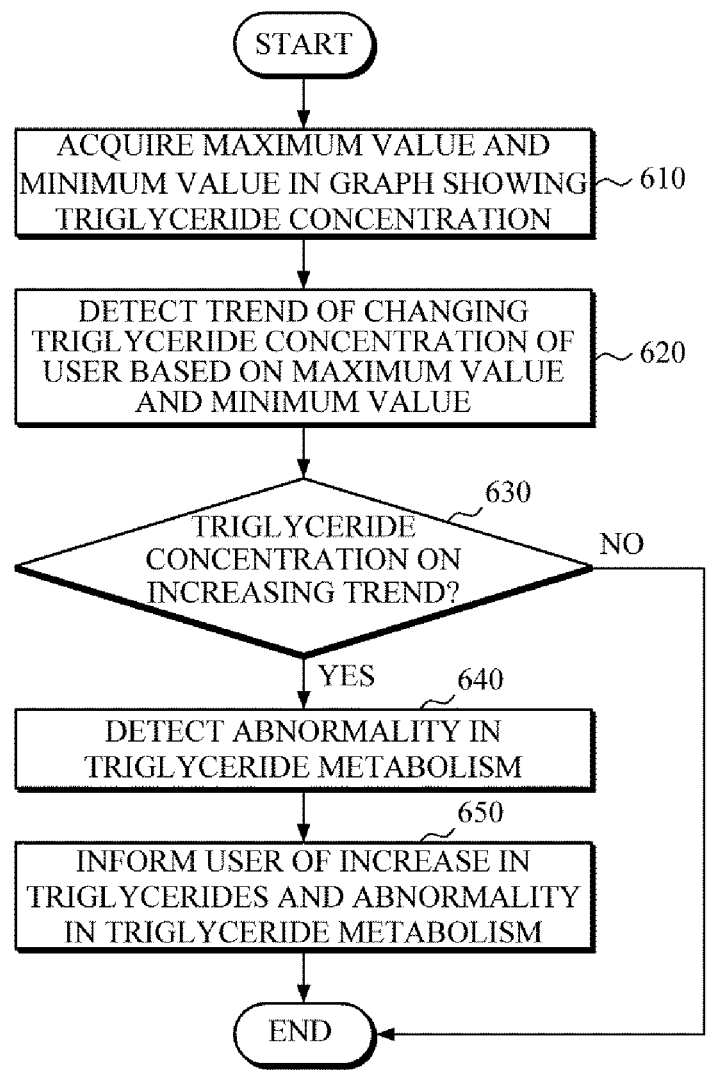
FIG. 6 is a flowchart illustrating a method for monitoring a user's health state according to another exemplary embodiment.

FIG. 6 is a flowchart of a method for monitoring a user's health state according to another exemplary embodiment.

The method for monitoring a user's health state of FIG. 6 is an exemplary embodiment performed by the user health state monitoring device 100 of FIG. 1.

The user health state monitoring device 100 may analyze a graph showing triglyceride concentrations based on measured data on triglycerides of a user and acquire a maximum value and a minimum value in the graph (operation S610). Then, the user health state monitoring device 100 may detect a trend of changing triglyceride concentration of a user based on changes in the acquired maximum value and minimum value (operation S620). Since an increase of the maximum value or the minimum value of triglycerides may occur temporarily, the user health state monitoring device 100 may determine that the user's triglyceride concentration has an increasing trend when the maximum value or the minimum value is increased continually for a period that is longer than a predetermined reference period.

When it is confirmed that the user's triglyceride concentration has an increasing trend (operation S630), the user health state monitoring device 100 may detect that there is an abnormality in triglyceride metabolism (operation S640). In addition, the user health state monitoring device 100 may inform the user of the increasing trend of triglycerides and inform the user that there is an abnormality in the user's triglyceride metabolism through, for example, a display, a speaker, and/or a vibrator. (operation S650).

Figure 7:
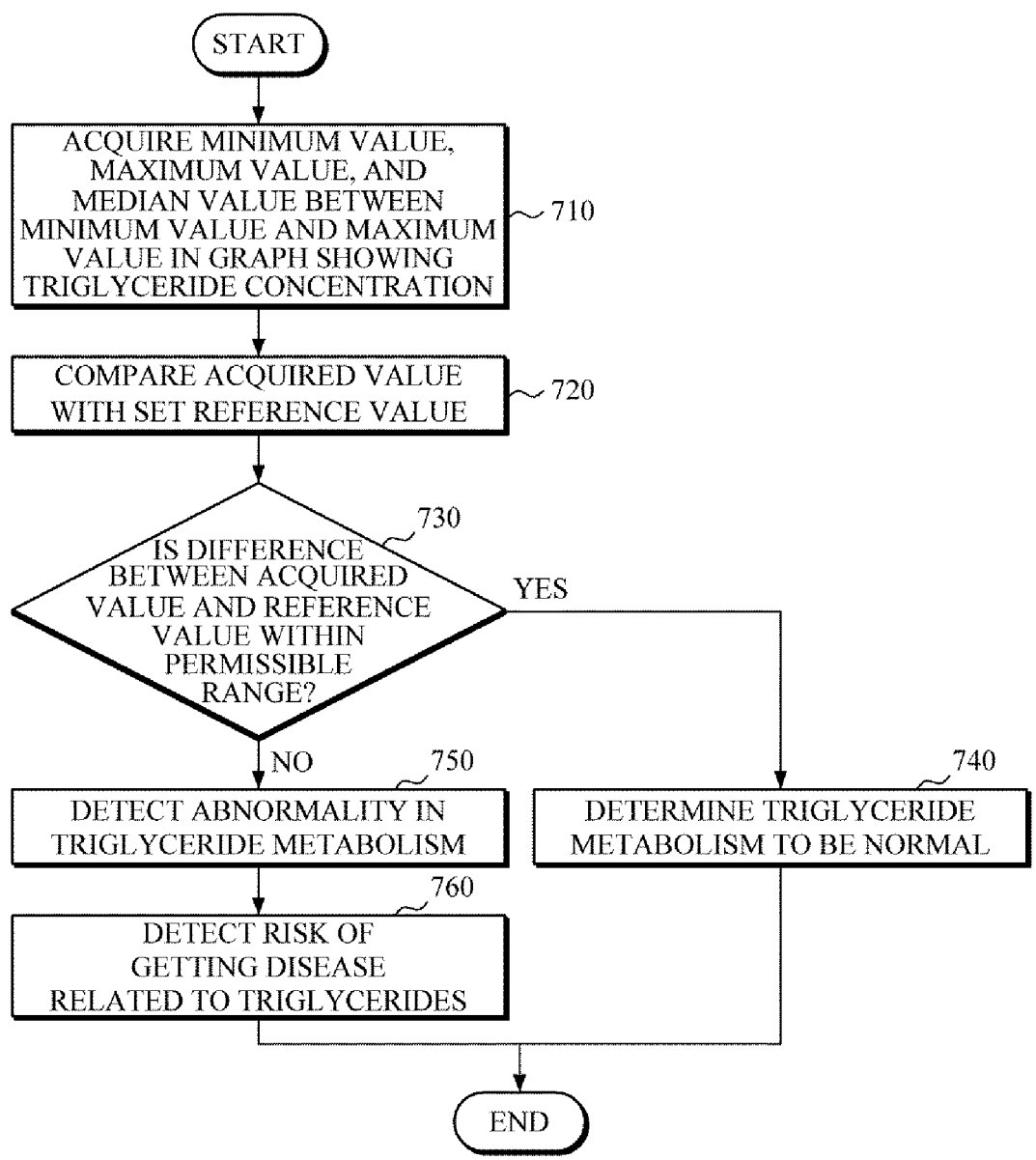
FIG. 7 is a flowchart illustrating a method for monitoring a user's health state according to still another exemplary embodiment.

FIG. 7 is a flowchart of a method for monitoring a user's health state according to still another exemplary embodiment.

The method for monitoring a user's health state of FIG. 7 is an embodiment performed by the user health state monitoring device 100 of FIG. 1.

The user health state monitoring device 100 may analyze a graph showing triglyceride concentrations based on measured data on triglycerides of a user, acquire a maximum value and a minimum value in the graph, and acquire a median value of the minimum value and the maximum value based on the maximum value and the minimum value in the graph (operation S710).

The user health state monitoring device 100 may compare the acquired minimum value, maximum value, and median value of the minimum value and the maximum value with preset reference values (operation S720) and, as a result of comparison, determine whether differences between the acquired minimum value, maximum value, and median value and the reference values are within permissible ranges (operation S730).

According to an aspect, the user health state monitoring device 100 may determine the user's triglyceride metabolism as normal when the difference between the acquired value and the reference value is within the permissible range (operation S740).

According to another aspect, the user health state monitoring device 100 may detect that there is an abnormality in the triglyceride metabolism when the difference between the acquired value and the reference value exceeds the permissible range (operation S750) and may detect a risk for the user getting diseases related to triglyceride such as arteriosclerotic disease and hypertriglyceridemia (operation S760).

Figure 8:
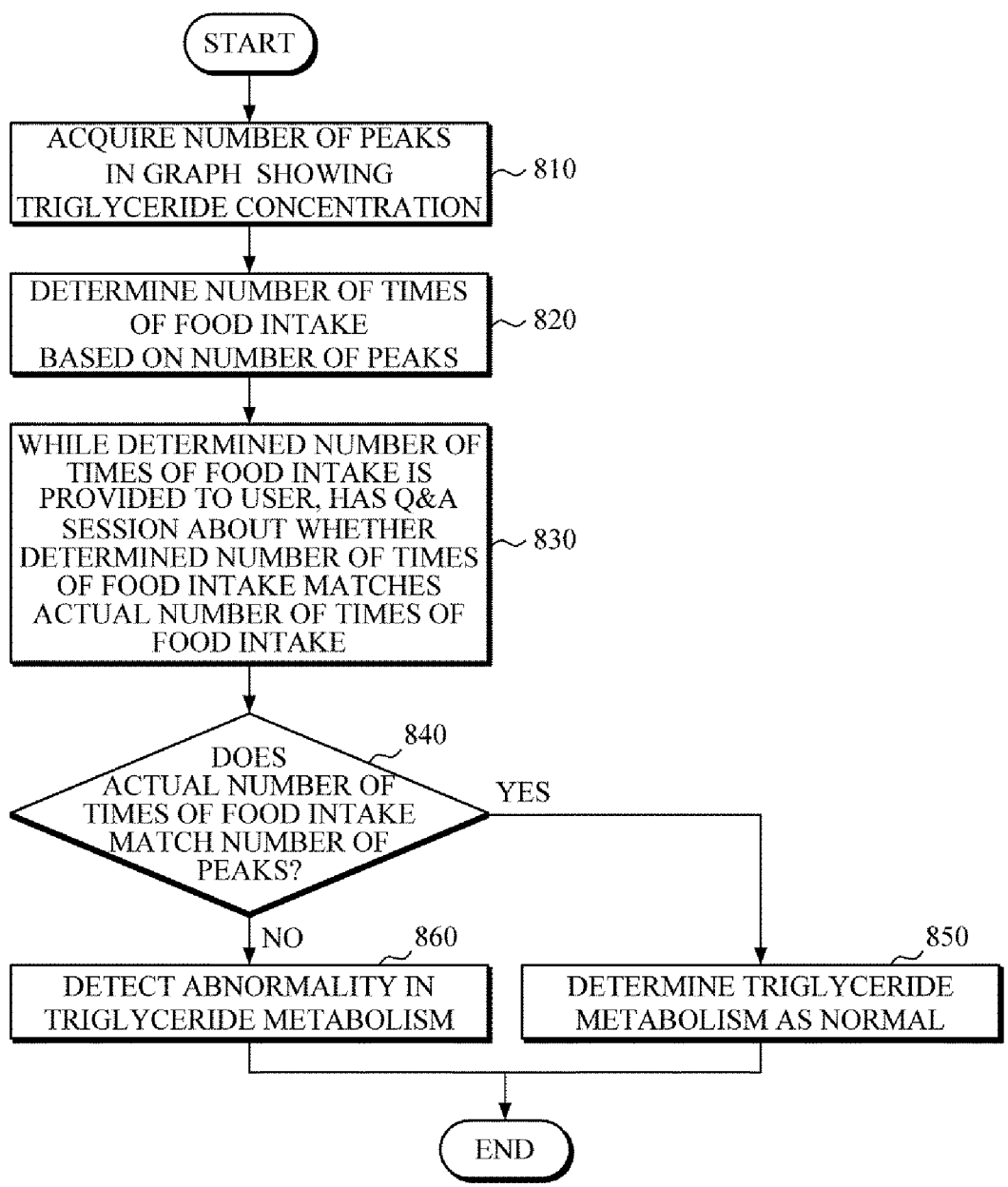
FIG. 8 is a flowchart illustrating a method for monitoring a user's health state according to still another exemplary embodiment.

FIG. 8 is a flowchart of a method for monitoring a user's health state according to still another exemplary embodiment.

The method for monitoring a user's health state of FIG. 8 is an exemplary embodiment performed by the user health state monitoring device 100 of FIG. 1.

The user health state monitoring device 100 may analyze a graph showing triglyceride concentrations based on measured data on triglycerides of a user based on an inflection point at which a positive slope of the graph changes back to a negative slope and acquire the number of peaks in the graph (operation S810).

When the number of peaks is acquired, the user health state monitoring device 100 may determine that the number of peaks in the graph is the number of times of food intake of the user (operation S820). Then, the user health state monitoring device 100 may have a Q&A session through, for example, a display and/or a voice device, in which the user health state monitoring device 100 may determine whether the determined number of times of food intake matches the actual number of times the user has ingested food. (operation S830).

When it is confirmed as a result of the Q&A session that the number of times of food intake determined by the user health state monitoring device 100 matches the actual number of times the user has ingested food, the user health state monitoring device 100 may determine the user's triglyceride metabolism to be normal (operation S850). When it is confirmed that the number of times of food intake determined by the user health state monitoring device 100 does not match the actual number of times the user has ingested food, the user health state monitoring device 100 may determine the user's triglyceride metabolism to be abnormal (operation S860).

Figure 9:
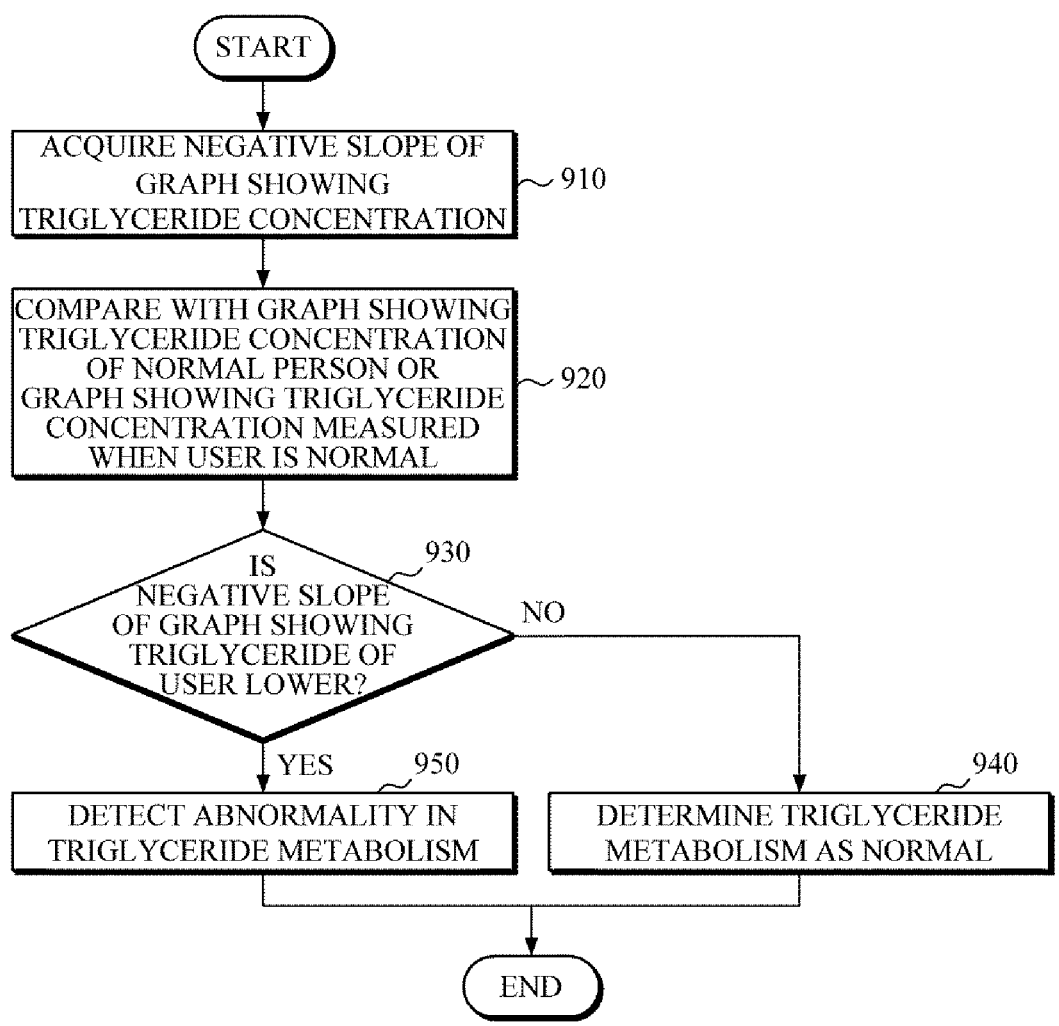
FIG. 9 is a flowchart illustrating a method for monitoring a user's health state according to still another exemplary embodiment.

FIG. 9 is a flowchart of a method for monitoring a user's health state according to still another exemplary embodiment.

The method for monitoring a user's health state of FIG. 9 is an exemplary embodiment performed by the user health state monitoring device 100 of FIG. 1.

The user health state monitoring device 100 may analyze a graph showing triglyceride concentrations based on measured data on triglycerides of a user and acquire a negative slope of the graph that shows an extent to which triglycerides in the body are cleared (operation S910).

The user health state monitoring device 100 may compare the graph showing triglyceride concentrations of the user with a sample graph showing triglyceride concentrations of a normal person or with a sample graph showing triglyceride concentrations measured in advance when the user in a normal state (operation S920). According to an aspect, when the negative slope of the graph showing triglyceride concentrations of the user is found to be higher as a result of comparison, since this means that triglyceride clearance is smoothly occurring in the user's body, the user health state monitoring device 100 may determine the user's triglyceride metabolism as normal (operation S940). According to another aspect, when the negative slope of the graph showing triglyceride concentrations of the user is found to be lower as a result of comparison, since this means that a speed of triglyceride clearance occurring in the user's body is slow, the user health state monitoring device 100 may detect that the user's triglyceride metabolism is abnormal (operation S950).

Figure 10:
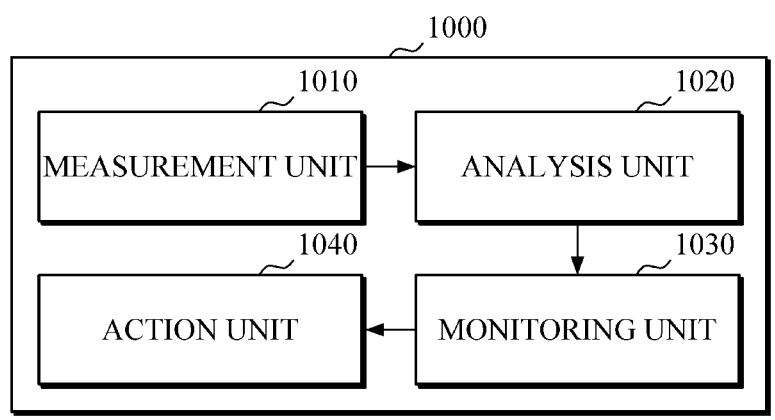
FIG. 10 is a block diagram illustrating a device for managing a user's health state according to another exemplary embodiment.

FIG. 10 is a block diagram of a device for managing a user's health state according to another exemplary embodiment.

Referring to FIG. 10, a user health state monitoring device 1000 may include a measurement unit 1010, an analysis unit 1020, a monitoring unit 1030, and an action unit 1040.

Since the measurement unit 1010, the analysis unit 1020, and the monitoring unit 1030 have been described with reference to FIG. 1, detailed descriptions thereof will be omitted.

The measurement unit 1010 may continuously measure data on triglycerides of a user during a predetermined period. The analysis unit 1020 may analyze a graph showing triglyceride concentrations based on continuously measured data on triglycerides to acquire analytical information that includes one or more of minimum values, maximum values, an average of the minimum values, an average of the maximum values, median values of the minimum values and the maximum values, number of peaks, intervals between the peaks, areas under graphs, and slopes of the graphs. The monitoring unit 1030 may monitor the user's health state based on the acquired analytical information.

The action unit 1040 may take a predetermined action based on the detected health state. According to an exemplary embodiment, when the monitoring unit 1030 detects that there is an abnormality in the user's health state, the action unit 1040 may generate an alarm signal. According to an aspect, the user health state monitoring device 1000 may provide an alarm which is, for example, a warning to a user that a triglyceride concentration has increased when an increase in the triglyceride concentration of the user is detected for a case in which triglyceride concentration is required to be managed, e.g., when the user suffers from a disease related to triglycerides such as hypertriglyceridemia.

The alarm signal of the action unit 1040 may include one or more of vibration, sound, and a visual signal. The action unit 1040 may generate a prerecorded human voice or a voice generated by software that reads letters including content that there is an abnormality in the health state as an alarm signal and may generate sound effects such as an alarm sound, an emergency bell, and/or short music.

The user health state management device 1000 may further include a display unit that displays one or more data sets on triglycerides, analytical information, and health states. According to an aspect, the display unit may visually provide an alarm signal generated from the action unit 1040. The display unit may include a desktop type or wall-mounted type display such as a TV and a computer monitor according to another aspect and may include a wearable device such as a wristwatch according to still another aspect.

According to another exemplary embodiment, the action unit 1040 may administer a drug that has an effect of accelerating triglyceride clearance or lowering a triglyceride concentration in consideration of data on triglycerides of the user into the user's body or may transfuse blood with low triglyceride concentration to the user.

Figure 11:
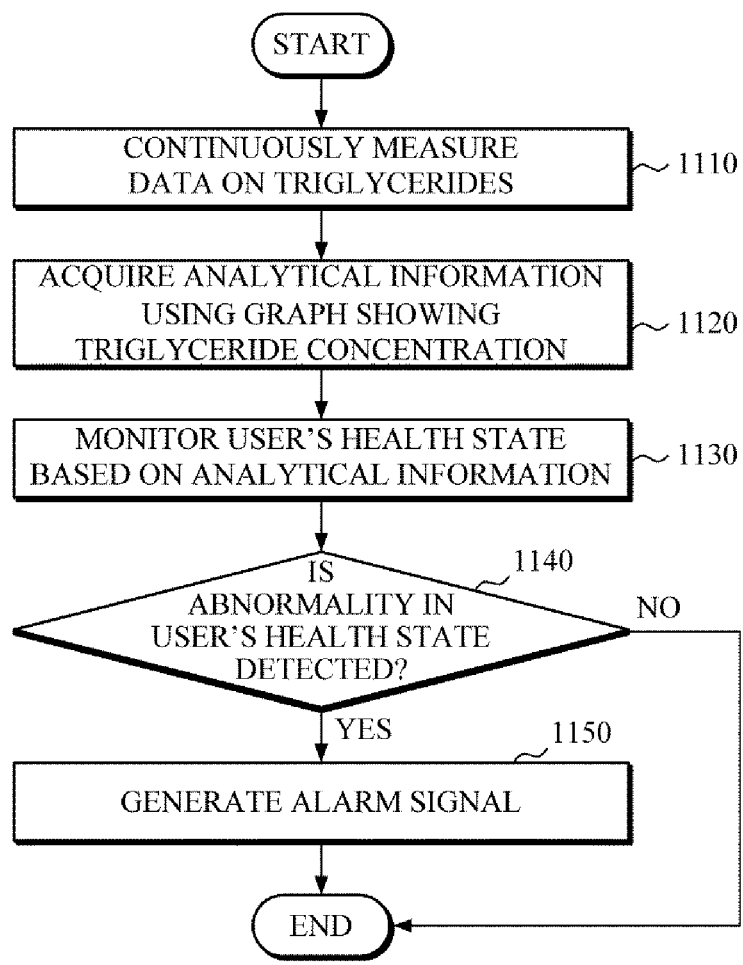
FIG. 11 is a flowchart illustrating a method for managing a user's health state according to another exemplary embodiment.

FIG. 11 is a flowchart of a method for managing a user's health state according to another exemplary embodiment.

The method for managing a user's health state of FIG. 11 is an exemplary embodiment performed by the user health state management device 1000 of FIG. 10.

The user health state management device 1000 may continuously measure data on triglycerides of a user during a predetermined period (operation S1110). The user health state management device 1000 may analyze a graph showing triglyceride concentrations based on the continuously measured data on triglycerides to acquire analytical information that includes one or more data sets including maximum values, minimum values, the number of peaks, intervals between the peaks, areas under graphs, and slopes of the graphs (operation S1120). The user health state management device 1000 may monitor the user's health state based on the acquired analytical information. (operation S1130).

The user health state management device 1000 may determine whether the user's health state is normal or abnormal (operation S1140). The user health state management device 1000 may perform a predetermined action such as generating an alarm signal when the detected health state is abnormal (operation S1150).

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A device for monitoring a triglyceride-related health state of a user, the device comprising:
   one or more processors configured to:
   continuously measure, for a predetermined period, a triglyceride concentration level of the user in a non-fasting state to generate a graph showing the triglyceride concentration level;
   analyze the graph showing the triglyceride concentration level to acquire analytical information comprising a number of peaks and intervals between the peaks of the graph; and
   determine the health state of the user based on at least one of the number of the peaks and the intervals between the peaks.

2. The device of claim 1, wherein the one or more processors are further configured to determine a diet pattern of the user based on at least one of the number of the peaks and the intervals between the peaks, and monitor the health state based on the determined diet pattern.

3. The device of claim 2, wherein the one or more processors are further configured to determine a number of times of food intake of the user based on the number of peaks, and determine time intervals in which the user has ingested food based on the intervals between the peaks, and determine whether the determined diet pattern of the user is normal.

4. The device of claim 2, wherein the one or more processors are further configured to provide a question and answer (Q&A) session about the diet pattern with the user based on the determined diet pattern, and determine the health state based on a correlation between responses of the user and at least one of the number of peaks and intervals between the peaks of the graph.

5. The device of claim 1, wherein the one or more processors are further configured to compare the graph showing the triglyceride concentration level of the user during the predetermined period with a reference graph showing a triglyceride concentration level of a healthy person, detect changes in the number of peaks and the intervals between the peaks acquired for each predetermined section, and determine whether the graph showing the triglyceride concentration level of the user has a normal pattern or an abnormal pattern.

6. The device of claim 1, wherein the one or more processors are further configured to determine the health state based on the acquired analytical information further including at least one of areas under the graph, and slopes of the graph.

7. The device of claim 6, wherein the one or more processors are further configured to determine a decreasing rate of the triglyceride concentration level based on a negative slope of the graph showing the triglyceride concentration level of the user.

8. The device of claim 6, wherein the one or more processors are further configured to monitor a triglyceride intake pattern of the user based on an increase or a decrease of the area under the graph.

9. The device of claim 1, wherein:
the predetermined period includes at least one of days, weeks, months, and years; and
the one or more processors are further configured to analyze the graph showing the triglyceride concentration level by dividing the graph into two or more sections which are shorter than the predetermined period.

10. A method for monitoring a triglyceride-related health state of a user, the method comprising:
continuously measuring, for a predetermined period, a triglyceride concentration level of the user in a non-fasting state to generate a graph showing the triglyceride concentration level;
analyzing the graph showing the triglyceride concentration level to acquire analytical information comprising a number of peaks and intervals between the peaks of the graph; and
determining the health state of the user based on at least one of the number of the peaks and the intervals between the peaks.

11. The method of claim 10, wherein the determining the health state further comprises: determining a diet pattern of the user based on at least one of the number of the peaks and the intervals between the peaks, and monitoring the health state based on the determined diet pattern.

12. The method of claim 11, wherein the determining the health state further comprises: determining a number of times of food intake of the user based on the number of peaks, and determining time intervals in which the user has ingested food based on the intervals between the peaks, and determining whether the determined diet pattern of the user is normal.

13. The method of claim 11, wherein the determining the health state further comprises: providing a question and answer (Q&A) session about the diet pattern with the user based on the determined diet pattern, and determining the health state based on a correlation between responses of the user and at least one of the number of peaks and intervals between the peaks of the graph.

14. The method of claim 10, wherein the determining the health state further comprises: comparing the graph showing the triglyceride concentration level of the user during the predetermined period with a reference graph showing a triglyceride concentration level of a healthy person, detecting changes in the number of peaks and the intervals between the peaks acquired for each predetermined section, and determining whether the graph showing the triglyceride concentration level of the user has a normal pattern or an abnormal pattern.

15. The method of claim 10, wherein the determining the health state further comprises: determine the health state based on the acquired analytical information further including at least one of areas under the graph, and slopes of the graph.

16. The method of claim 15, wherein the determining the health state further comprises: determining a decreasing rate of the triglyceride concentration level based on a negative slope of the graph showing the triglyceride concentration level of the user.

17. The method of claim 15, wherein the determining the health state further comprises: monitoring a triglyceride intake pattern of the user based on an increase or a decrease of the area under the graph.

* * * * *